US007477929B2

United States Patent
Klotz et al.

(10) Patent No.: US 7,477,929 B2
(45) Date of Patent: Jan. 13, 2009

(54) METHOD FOR FORECASTING THE CONTRAST MEDIUM FLOW IN A LIVING BODY

(75) Inventors: Ernst Klotz, Uttenreuth (DE); Annabella Rauscher, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 69 days.

(21) Appl. No.: 11/352,227

(22) Filed: Feb. 13, 2006

(65) Prior Publication Data

US 2006/0239917 A1    Oct. 26, 2006

(30) Foreign Application Priority Data

Feb. 14, 2005    (DE) .................. 10 2005 006 657

(51) Int. Cl.
  *A61B 6/00* (2006.01)
  *A61B 5/05* (2006.01)
(52) U.S. Cl. ............... 600/431; 600/420; 600/419
(58) Field of Classification Search ............. 600/419, 600/420, 431; 702/15, 84
  See application file for complete search history.

(56) References Cited

U.S. PATENT DOCUMENTS

| | | | |
|---|---|---|---|
| 5,840,026 A * | 11/1998 | Uber et al. | 600/431 |
| 6,195,579 B1 * | 2/2001 | Carroll et al. | 600/420 |
| 6,233,475 B1 * | 5/2001 | Kim et al. | 600/420 |
| 6,385,483 B1 * | 5/2002 | Uber et al. | 600/431 |
| 6,397,097 B1 * | 5/2002 | Requardt | 600/431 |
| 6,425,864 B1 * | 7/2002 | Foo et al. | 600/420 |
| 6,535,821 B2 * | 3/2003 | Wang et al. | 702/19 |
| 6,643,534 B2 * | 11/2003 | Foo et al. | 600/420 |

(Continued)

FOREIGN PATENT DOCUMENTS

DE    102 30 877 A1    2/2004

OTHER PUBLICATIONS

D.Fleischmann, K.Hittmair: "Mathematical Analysis of Arterial Enhancement and Optimization of Bolus Geometry for CT Angiography Using the Discrete Fourier Transform", In: Journal of Computer Assisted Tomography, 1999, vol. 23, No. 3, pp. 474-484.

(Continued)

*Primary Examiner*—Eric F Winakur
*Assistant Examiner*—Helene Bor
(74) *Attorney, Agent, or Firm*—Harness Dickey & Pierce (57) ABSTRACT

A method is disclosed for forecasting the contrast medium flow in a living body, in particular in a patient, in which a defined test bolus with a contrast medium is injected, preferably intravenously and with a known injection flow profile, into the body, preferably into a blood vessel. The time concentration profile of the contrast medium is observed and determined over a limited time period with a number of measuring instants at at least one location in the body with the aid of a tomographic method. The time profile of the contrast medium concentration of another contrast medium dose is forecast with the aid of a linear cause/effect formulation from the measured data obtained via the distribution of the contrast medium. The following calculation formula is then used for forecasting the time concentration profile $\tilde{c}_R(t)$ of the contrast medium at at least one of the previously measured locations of the body:

$$\tilde{c}_R(t) = \frac{1}{F_T} \sum_{n=na}^{n=ne} \int_{x=xa}^{x=xe} dt' \tilde{c}_R(t + t_{0T} - n\Delta_T - t') b'_R(t').$$

18 Claims, 5 Drawing Sheets

U.S. PATENT DOCUMENTS

| | | | | |
|---|---|---|---|---|
| 2001/0056233 A1* | 12/2001 | Uber et al. | | 600/431 |
| 2002/0010551 A1* | 1/2002 | Wang et al. | | 702/19 |
| 2002/0091316 A1* | 7/2002 | Foo et al. | | 600/420 |
| 2002/0111550 A1* | 8/2002 | Schwamm et al. | | 600/419 |
| 2004/0008028 A1 | 1/2004 | Horger et al. | | |
| 2004/0064040 A1* | 4/2004 | Masuda et al. | | 600/431 |
| 2005/0090736 A1* | 4/2005 | Sommer | | 600/425 |
| 2006/0178836 A1* | 8/2006 | Bai et al. | | 702/19 |
| 2006/0239918 A1* | 10/2006 | Klotz et al. | | 424/9.3 |
| 2007/0112264 A1* | 5/2007 | Wu et al. | | 600/410 |
| 2007/0135710 A1* | 6/2007 | Braess | | 600/431 |

OTHER PUBLICATIONS

German Office Action Issued on Jan. 25, 2006.

* cited by examiner

METHOD FOR FORECASTING THE CONTRAST MEDIUM FLOW IN A LIVING BODY

The present application hereby claims priority under 35 U.S.C. §119 on German patent application number DE 10 2005 006 657.7 filed Feb. 14, 2005, the entire contents of which is hereby incorporated herein by reference.

FIELD

The invention generally relates to a method for forecasting the contrast medium flow in a living body, for example in a patient. In at least one embodiment, it generally relates to a method in which a defined test bolus with a contrast medium is injected, for example intravenously and with a known injection flow profile, into the body, for example into a blood vessel, the time concentration profile of the contrast medium is observed and determined over a limited time period Z with a number of measuring instants at at least one location in the body with the aid of a tomographic method. Further, the time profile of the contrast medium concentration of another contrast medium dose is forecast from the measured data obtained via the distribution of the contrast medium with the aid of a linear cause/effect formulation.

BACKGROUND

In tomographic methods, particularly in the field of computed tomography or NMR tomography, it is advantageous to apply contrast media in order to display specific body regions because of the low contrasts in the display that occur there, and thereby to obtain a more contrasting image of these body regions. However, contrast media mostly have the disadvantage that they are biologically incompatible and that their dose therefore has to be kept as low as possible. Because of the biological variability of the bodies under examination, however, it is impossible to make a sufficiently accurate and generally valid statement as to how the concentration profile of a specific contrast medium dose will develop over time at an observed location in the body. It is therefore necessary in the case of each body under examination to make a test injection of a contrast medium or test bolus dose so as to observe the effect thereof, in particular the subsequent time profile of the concentration values at the location of interest in the body to be examined.

In the case of application in association with a CT examination, the concentration is measured indirectly over a specific time period after the test bolus injection and with the use of the smallest possible radiation doses, this being done via the changes in the HU values resulting there. Since only the imaging effect of the contrast medium is of interest, and there is a linear relationship between the imaging effect and concentration of the contrast medium, a statement on the absolute concentration of the contrast medium remains open and trivial. Again, the resolving power of the images of such a test examination remains slight.

It is known to use knowledge of the effect of such a test bolus dose with the aid of a Fourier transformation as a basis for preliminary calculation of the effect of a correct contrast medium dose, and thus for determining the absolutely necessary dose of contrast medium.

SUMMARY

It is an object of at least one embodiment of the invention to find an improved forecasting method. As such, it can be possible to make a better forecast of the absolutely necessary contrast medium dose for examining a specific body region.

The inventors have realized the following:

Thus, in accordance with at least one embodiment, an aim is to find an improved method that forecasts the time profile of enhancement values at the same point using a further, different injection protocol from the time profile of the enhancement values after a test bolus injection. This is intended to serve the purpose of planning an optimal contrast medium protocol. Here, enhancement values are understood as the effects of the concentration changes of the contrast medium on the pictorial display. A CT examination is thus the HU values determined, for example.

The profile of the test bolus can be represented by the following linear function:

$$b_T(t) = F_T \Theta(t - t_{0T}) \Theta(t_{FT} - t), \quad (1)$$

$F_T$ representing the flow rate, $t_{0T}$ the starting time and $t_{FT}$ the end time of the test bolus $b_T(t)$. Here, $\Theta(t)$ designates the Heaviside or so-called step function, that is defined as follows:

$$\Theta(t) = \begin{cases} 1 & \text{for } t > 0 \\ 0 & \text{for } t < 0. \end{cases} \quad (2)$$

The quantity of contrast medium consumed is then yielded as $F_T(t_{FT} - t_{0T})$. The profile of the enhancement values $c_T(t)$ at the prescribed point owing to the dose of a test bolus is given by $$c_T(t) = c_0 + \tilde{c}_T(t) \quad (3)$$

in the case of a CT examination the HU value without a contrast medium dose being designated by $c_0$, and $\tilde{c}_T(t)$ being the component caused by the contrast medium. These data can now be used to forecast the profile of the enhancement values $c_R(t)$ for providing a dose of a correct bolus, that is to say one used for the examination, at the same point $$c_R(t) = c_0 + \tilde{c}_R(t), \quad (4)$$

when an altered contrast medium bolus $b_R(t)$ with $$b_R(t) = F_R \Theta(t - t_{0R}) \Theta(t_{FR} - t), \quad (5)$$

is applied or injected.

It is known to deduce the correct bolus dose, and the contrast medium concentration resulting therefrom, by simply adding up the measured test bolus curve in a way offset according to the lengthened bolus injection time. At least one embodiment of this method certainly functions very reliably, but it has the disadvantage that the duration of the contrast medium flow is limited to integral multiples of the duration of the test bolus.

It is likewise known to apply a Fourier transformation of the measured test bolus curve in order to deduce the effect of the correct bolus dose. By diverting via the Fourier transform of the test bolus curve, it is possible to circumvent the limitation of the duration to integral multiples of the duration of the test bolus. Since, however, the test bolus curve generally comprises a few, very noisy data points, the calculation of the Fourier transform is numerically extremely unstable and thus unsuitable for data that are recorded in everyday clinical practice.

Moreover, the problems arise with these methods when the test bolus data do not embrace the entire enhancement curve, that is to say have been scanned too early or too late. Since, in addition, the recirculation of the contrast medium plays an important role for a stable forecast, there would actually be a need to make a very long measurement of the test bolus for the methods.

According to at least one embodiment of the invention, at least one of these problems may be lessened or even avoided as follows by way of a different calculation method that is based on a linear cause/effect relationship. In addition, a physiological model can be used for forecasting for examination time periods not measured during the test run.

Forecasting by using a simple linear formulation:

An essential assumption of this method of at least one embodiment, is the linearity between cause (=contrast medium dose) and effect (=the increase in the HU values in the case of the CT examination). This assumption may be expressed mathematically by the following relationship $$\tilde{c}(t) = \int_{-\infty}^{\infty} dt' k(t-t') b(t'), \tag{6}$$

b designating bolus curves below, and c contrast medium curves. Here, k is an arbitrary patient-specific function and describes the response of the respective body to the injection of the contrast medium.

A consideration of the Fourier transformation of this equation yields $$\tilde{C}(\xi) = K(\xi) B(\xi), \tag{7}$$

the Fourier transform of a function $f(t)$ being given here by $$F(\xi) = \int_{-\infty}^{\infty} dt f(t) \exp(i\xi t) \tag{8}$$

The relationship (7) holds both for the test bolus and for the bolus to be forecast. The test bolus is used in order to determine $K(\xi)$, $\xi$ being the variable in Fourier space corresponding to time $$K(\xi) = \frac{\tilde{C}_T(\xi)}{B_T(\xi)}, \tag{9}$$

so that then $\tilde{c}_R(\xi)$, the Fourier transform of the concentration profile, can be determined with the aid of the following formula $$\tilde{C}_R(\xi) = \frac{B_R(\xi)}{B_T(\xi)} \tilde{C}_T(\xi). \tag{10}$$

The function $\tilde{c}_R(\xi)$ being sought then results therefrom by way of the inverse Fourier transformation $$f(t) = \frac{1}{2\pi} \int_{-\infty}^{\infty} d\xi F(\xi) \exp(-i\xi t) \tag{11}$$

This procedure is used in general in order to determine the contrast medium profile via a Fourier transformation. Since the Fourier transform of the test bolus is known, however, it is thereby possible to forecast the contrast medium profile for an arbitrary, different rectangle of a bolus injection, but also for entirely arbitrary contrast medium injections. Here, "rectangle" is to be understood as a constant flow of contrast medium during the injection over a specific time that is represented as a rectangle when plotted graphically and in an idealized fashion. The detailed derivation follows for an arbitrary different rectangle, and the end result for arbitrary injection curves.

The Fourier transformation of the two boli (1) and (5) is given by $$B_I(\xi) = F_I \frac{1}{i\xi} (\exp(i\xi t_{FI}) - \exp(i\xi t_{0I})), \tag{12}$$

so that the Fourier transform of the enhancement curve being sought results as $$\tilde{C}_R(\xi) = \frac{F_R}{F_T} \frac{\exp(i\xi t_{FR}) - \exp(i\xi t_{0R})}{\exp(i\xi t_{FT}) - \exp(i\xi t_{0T})} \tilde{C}_T(\xi). \tag{13}$$

The enhancement curve being sought is then given by $$\tilde{c}_R(t) = \frac{1}{2\pi} \frac{F_R}{F_T} \int_{-\infty}^{\infty} d\xi \exp(-i\xi t) \frac{\exp(i\xi t_{FR}) - \exp(i\xi t_{0R})}{\exp(i\xi t_{FT}) - \exp(i\xi t_{0T})} \tilde{C}_T(\xi). \tag{14}$$

This expression can be integrated without further knowledge of the Fourier transform $\tilde{c}_-(\xi)$ by developing the phase factor occurring $$\frac{\exp(i\xi t_{FR}) - \exp(i\xi t_{0R})}{\exp(i\xi t_{FT}) - \exp(i\xi t_{0T})} = \frac{\exp(i\xi t_{0R}) 1 - \exp(i\xi \Delta_R)}{\exp(i\xi t_{0T}) 1 - \exp(i\xi \Delta_T)} \tag{15}$$

$$= \frac{\exp(i\xi t_{0R})}{\exp(i\xi t_{0T})} (1 - \exp(i\xi \Delta_R))$$

$$\sum_{n=0}^{\infty} (\exp(i\xi \Delta_T))^n$$

$$= \frac{\exp(i\xi t_{0R})}{\exp(i\xi t_{0T})} (1 - \exp(i\xi \Delta_R))$$

$$\sum_{n=0}^{\infty} \exp(in\xi \Delta_T),$$

the abbreviation $\Delta_I = t_{FI} - t_{0I}$ having been used. The result is therefore $$\tilde{c}_R(t) = \frac{1}{2\pi} \frac{F_R}{F_T} \int_{-\infty}^{\infty} d\xi \exp(-i\xi(t - t_{0R} + t_{0T})) \tag{16}$$

$$(1 - \exp(i\xi \Delta_R)) \sum_{n=0}^{\infty} \exp(in\xi \Delta_T) \tilde{C}_T(\xi)$$

$$= \frac{1}{2\pi} \frac{F_R}{F_T} \sum_{n=0}^{\infty} \int_{-\infty}^{\infty} d\xi (1 - \exp(i\xi \Delta_R))$$

$$\exp(-i\xi(t - t_{0R} + t_{0T} + n\Delta_T)) \tilde{C}_T(\xi)$$

$$= \frac{F_R}{F_T} \sum_{n=0}^{\infty} (\tilde{c}_T(t - t_{0R} + t_{0T} - n\Delta_T) -$$

$$\tilde{c}_T(t - t_{FR} + t_{0T} - n\Delta_T)).$$

The infinite sum occurring is no problem for the concrete calculation, since the response function occurring for the test bolus $\tilde{c}(t)$ is, after all, assumed to vanish before and after a certain instant, that is to say as long as there is still no bolus flowing, or else long after the injection it should also be impossible to observe an enhancement. Consequently, only a finite number of terms of the sum need be added up in practice.

Again, this formula constitutes the generalization of the simple addition when the duration of the contrast medium profile to be forecast is a non-integral multiple of the duration of the test bolus; for integral multiples it reduces to a simple sum in which the test bolus curve is added up with a time offset.

For general contrast medium profiles $b_R(t)$ results analogous to this $$\tilde{c}_R(t) = \frac{1}{2\pi} \frac{i}{F_T} \int_{-\infty}^{\infty} d\xi \xi \exp(-i\xi t) \frac{B_R(\xi)}{\exp(i\xi t_{FT}) - \exp(i\xi t_{0T})} \tilde{C}_T(\xi). \quad (17)$$

By developing the denominator and utilizing the fact that $$FT(b'_R)(\xi) = -i\xi B_R(\xi) \quad (18)$$

it follows that $$\tilde{c}_R(t) = \frac{1}{2\pi} \frac{1}{F_T} \sum_{n=0}^{\infty} \int_{-\infty}^{\infty} d\xi \exp(-i\xi(t + t_{0T} - n\Delta_T)) FT(b'_R)(\xi) \tilde{C}_T(\xi) \quad (19)$$

$$= \frac{1}{F_T} \sum_{n=0}^{\infty} \int_{-\infty}^{\infty} dt' \tilde{c}_T(t + t_{0T} - n\Delta_T - t') b'_R(t'), \quad (20)$$

and so even in the case of an arbitrary contrast medium profile there is a need only for the data and not for their Fourier transform.

At least one embodiment of this method can be used to cover substantially forecasting time periods that have been measured previously by means of measured values on the basis of test bolus doses. However, if it is desired nevertheless to forecast beyond the instant of abortion of the test measurement, the inventors propose making additional use of a simple physiological model and obtaining the forecast values therefrom.

Use is made for this purpose of the following defining differential equation of a physiological system:

$$\frac{\partial}{\partial t} b(x, t) + v \frac{\partial}{\partial x} b(x, t) - D \frac{\partial^2}{\partial x^2} b(x, t) = F \delta^{(1)}(x) \Theta(t - t_0) \Theta(t_F - t), \quad (21)$$

in which the left-hand side is a one-dimensional thermal conduction equation that is supplemented by a source term on the right-hand side.

The source term on the right-hand side describes the test bolus, F designating the flow rate and $t_0$ and $t_F$ designating the starting time and end time, respectively, under consideration. The one-dimensional delta function $\delta^{(1)}(x)$ in this case describes the puncture point of the injection at the initial location 0. The left side is determined essentially by two processes: the contrast medium is transported at the drift velocity v, and at the same time the initially rectangular test bolus diffuses with the diffusion constant D. Here, the diffusion constant D essentially describes travel time differences, and/or simulates fluctuations in the blood velocity.

The solution to this differential equation is given by determining the Greens function of the differential operator $$\left( \frac{\partial}{\partial t} + v \frac{\partial}{\partial x} - D \frac{\partial^2}{\partial x^2} \right) G(x - x', t - t') = \delta^{(1)}(x - x') \delta^{(1)}(t - t'), \quad (22)$$

which means that the solution of the differential equation can then be shown directly as $$b(x,t) = \int_{-\infty}^{\infty} F \delta^{(1)}(x') \Theta(t' - t_0) \Theta(t_F - t') G(x - x', t - t') dt' dx' \quad (23)$$

The Greens function of the one-dimensional thermal conduction equation has the form of $$G(x - x', t - t') = \Theta(t - t') \frac{1}{\sqrt{4D(t - t')\pi}} \exp\left( -\frac{(x - x' - v(t - t'))^2}{4D(t - t')} \right) \quad (24)$$

which means that the solution of the differential equation is yielded as follows:

$$b(x, t) = \int_{-\infty}^{\infty} F \delta^{(1)}(x') \Theta(t' - t_0) \Theta(t_F - t') G(x, t : x', t') dt' dx' \quad (25)$$

$$= F \int_{-\infty}^{\infty} dt' \Theta(t' - t_0) \Theta(t_F - t') \Theta(t - t')$$

$$\frac{1}{\sqrt{4D(t - t')\pi}} \exp\left( -\frac{(x - v(t - t'))^2}{4D(t - t')} \right)$$

$$= F \Theta(t - t_0) \left( \Theta(t_F - t) \int_{t_0}^{t} dt' + \Theta(t - t_F) \int_{t_0}^{t_F} dt' \right)$$

$$\frac{1}{\sqrt{4D(t - t')\pi}} \exp\left( -\frac{(x - v(t - t'))^2}{4D(t - t')} \right)$$

$$= \frac{F}{2v} \Theta(t - t_0) \left( \Theta(t_F - t) \left( 1 - \exp\left(\frac{xv}{D}\right) + \exp\left(\frac{xv}{D}\right) \right) \right.$$

$$Erf\left( \frac{x + v(t - t_0)}{\sqrt{4D(t - t_0)}} \right) - Erf\left( \frac{x - v(t - t_0)}{\sqrt{4D(t - t_0)}} \right) \right) +$$

$$\Theta(t - t_F) \left( \exp\left(\frac{xv}{D}\right) Erf\left( \frac{x + v(t - t_0)}{\sqrt{4D(t - t_0)}} \right) - \left( \frac{x - v(t - t_0)}{\sqrt{4D(t - t_0)}} \right) - \right.$$

$$\left. \exp\left(\frac{xv}{D}\right) Erf\left( \frac{x + v(t - t_F)}{\sqrt{4D(t - t_F)}} \right) - Erf\left( \frac{x - v(t - t_F)}{\sqrt{4D(t - t_F)}} \right) \right) \right).$$

The error function $Erf$ is given in this case by $$Erf(x) = \frac{2}{\sqrt{\pi}} \int_{-\infty}^{x} \exp(-t^2) dt. \quad (26)$$

Since the error function has values not equal to ±1 only for values in the vicinity of the zero points of its argument, the solution for x>0 and v>0 can be approximated as follows:

$$b(x, t) = \frac{F}{2v} \Theta(t - t_0) \left( \Theta(t_F - t) \left( 1 - Erf\left( \frac{x - v(t - t_0)}{\sqrt{4D(t - t_0)}} \right) \right) \right) +$$

$$\Theta(t - t_F) \left( Erf\left( \frac{x - v(t - t_F)}{\sqrt{4D(t - t_F)}} \right) \right) - Erf\left( \frac{x - v(t - t_0)}{\sqrt{4D(t - t_0)}} \right) \right).$$

Thus, if the test bolus curve is described by $$b(x,t) = c_0 + C\Theta(t - t_{0T})\left(\Theta(t_{FT} - t)\left(1 - Erf\left(A\frac{B - (t - t_{0T})}{\sqrt{(t - t_{0T})}}\right)\right) + \right. \quad (27)$$
$$\left. \Theta(t - t_{FT})\left(Erf\left(A\frac{B - (t - t_{FT})}{\sqrt{(t - t_{FT})}}\right)\right) - Erf\left(A\frac{B - (t - t_{0T})}{\sqrt{(t - t_{0T})}}\right)\right),$$

the contrast medium curve being sought is given by $$b(x,t) = c_0 + C\frac{F_R}{F_T}\Theta(t - t_{0R})\left(\Theta(t_{FR} - t)\left(1 - Erf\left(A\frac{B - (t - t_{0R})}{\sqrt{(t - t_{0R})}}\right)\right) + \right. \quad (28)$$
$$\left. \Theta(t - t_{FR})\left(Erf\left(A\frac{B - (t - t_{FR})}{\sqrt{(t - t_{FR})}}\right)\right) - Erf\left(A\frac{B - (t - t_{0R})}{\sqrt{(t - t_{0R})}}\right)\right).$$

Thus, fitting the test bolus curve fixes the free parameters of the differential equation in order that they can then be used to make the forecast.

Alternatively, the physiological function can also be adapted within the scope of at least one embodiment of this invention with a gamma variance distribution, but the test bolus curve cannot be entirely completely described thereby.

In accordance with these basic ideas set forth above, the inventors propose, in at least one embodiment, to improve the method for forecasting the contrast medium flow in a living body, in particular in a patient, in which a defined test bolus with a contrast medium is injected, preferably intravenously and with a known injection flow profile, into the body, preferably into a blood vessel, the time concentration profile of the contrast medium is observed and determined over a limited time period Z with a number of measuring instants at at least one location in the body with the aid of a tomographic method, and the time profile of the contrast medium concentration of another contrast medium dose is forecast with the aid of a linear cause/effect formulation from the measured data obtained via the distribution of the contrast medium, to the effect that the following calculation formula is used for the linear model for forecasting the time concentration profile $\tilde{c}_R(t)$ of the contrast medium at at least one of the previously measured locations of the body:

$$\tilde{c}_R(t) = \frac{1}{F_T}\sum_{n=-\infty}^{\infty}\int_{-\infty}^{\infty}dt'\tilde{c}_R(t + t_{0T} - n\Delta_T - t')b'_R(t'),$$

in which
$\tilde{c}_R(t+t_{0T}-n\Delta_T-t')$ corresponds to the concentration displaced from the instant t to the instant $t+t_{0T}-n\Delta_T-t'$,
$F_T$ corresponds to the flow rate of the contrast medium of the test bolus,
$b'_R(t')$ corresponds to the time derivative of the profile of the contrast medium bolus administered,
t corresponds to the forecast instant, and
t' corresponds to the integration variable.

It is to be pointed out here that the specified limits of $-\infty$ to $+\infty$ are, of course, of a theoretical nature and can be replaced in practice by instants that are at an appropriate distance before and after the measurements.

In the case of the use of a contrast medium injection with constant flow over the injection time as test bolus and as correct bolus to be calculated, it is proposed to calculate the forecast of the concentration profile $\tilde{c}_R(t)$ with the aid of the following formula:

$$\tilde{c}_R(t) = \frac{1}{2\pi}\frac{F_R}{F_T}\int_{-\infty}^{\infty}d\xi\exp(-i\xi(t - t_{0R} + t_{0T}))$$
$$(1 - \exp(i\xi\Delta_R))\sum_{n=0}^{\infty}\exp(in\xi\Delta_T)\tilde{C}_T(\xi)$$
$$= \frac{1}{2\pi}\frac{F_R}{F_T}\sum_{n=0}^{\infty}\int_{-\infty}^{\infty}d\xi(1 - \exp(i\xi\Delta_R))$$
$$\exp(-i\xi(t - t_{0R} + t_{0T} + n\Delta_T))\tilde{C}_T(\xi)$$
$$= \frac{F_R}{F_T}\sum_{n=0}^{\infty}(\tilde{c}_T(t - t_{0R} + t_{0T} - n\Delta_T) -$$
$$\tilde{c}_T(t - t_{FR} + t_{0T} - n\Delta_T))$$

the following designations being used:
$F_T$ flow rate of the contrast medium of the test bolus
$F_R$ flow rate of the contrast medium of the correct bolus
$\xi$ integration variable
$t_{0R}$ starting instant of the correct bolus
$t_{0T}$ starting instant of the test bolus.

It can be advantageous in the case of the method according to at least one embodiment of the invention when, in addition, in order to forecast instants for which no measured values from a test bolus injection are present, the contrast medium concentration is forecast using a physiological calculation model.

In this case, the following system of differential equations is used as physiological calculation model:

$$\frac{\partial}{\partial t}b(x,t) + v\frac{\partial}{\partial x}b(x,t) - D\frac{\partial^2}{\partial x^2}b(x,t) = F\delta^{(1)}(x)\Theta(t - t_0)\Theta(t_F - t),$$

the following designations being used:
b(x,t) concentration profile of the bolus at location x at time t,
F flow of the contrast medium,
$\delta^{(1)}$ delta function,
$\Theta(t-t_0)$ Heaviside step function for describing the beginning of the contrast medium injection,
$\Theta(t_F-t)$ Heaviside step function for describing the end of the contrast medium injection.

In accordance with this physiological model, in order to forecast instants for which no measured values from a test bolus injection are present, the measured concentration profile can be firstly approximated after a test bolus injection with the aid of the following function:

$$b(x,t) = c_0 + C\Theta(t - t_{0T})\left(\Theta(t_{FT} - t)\left(1 - Erf\left(A\frac{B - (t - t_{0T})}{\sqrt{(t - t_{0T})}}\right)\right) + \right.$$
$$\left. \Theta(t - t_{FT})\left(Erf\left(A\frac{B - (t - t_{FT})}{\sqrt{(t - t_{FT})}}\right)\right) - Erf\left(A\frac{B - (t - t_{0T})}{\sqrt{(t - t_{0T})}}\right)\right)$$

and subsequently the expected concentration profile is estimated using the parameters A, B, C and c_0 thus calculated with the aid of the following formula:

$$b(x, t) = c_0 + C\frac{F_R}{F_T}\Theta(t - t_{0R})\left(\Theta(t_{FR} - t)\left(1 - Erf\left(A\frac{B - (t - t_{0R})}{\sqrt{(t - t_{0R})}}\right)\right) + \Theta(t - t_{FR})\left(Erf\left(A\frac{B - (t - t_{FR})}{\sqrt{(t - t_{FR})}}\right) - Erf\left(A\frac{B - (t - t_{0R})}{\sqrt{(t - t_{0R})}}\right)\right)\right)$$

the following designations being used:

A first function constant, substantially indirectly proportional to the width of the test bolus curve,
B second function constant, substantially proportional to the peak of the test bolus curve,
b(x,t) concentration profile of the bolus at location x at time t,
C third function constant, proportional to the area under the test bolus curve,
$c_0$ enhancement value before the injection of the contrast medium bolus,
Erf( ) error function,
$F_R$ flow rate of the contrast medium of the correct bolus,
$F_T$ flow rate of the contrast medium of the test bolus,
$t_{FR}$ final instant of the correct bolus,
$t_{FT}$ final instant of the test bolus,
$t_{0R}$ starting instant of the correct bolus,
$t_{0T}$ starting instant of the test bolus,
x observed location,
$\Theta$ Heaviside step functions for describing the beginning and the end of the bolus injections.

If forecasts both from the linear model and from the physiological model are present for forecast instants, it is also possible to use a simple mean value of the two forecast values or a weighted mean value of the two forecast values.

BRIEF DESCRIPTION OF THE DRAWINGS

Embodiments of the invention are explained in more detail below with the aid of the detailed description and figures with reference to an example embodiment, the following designations being used: 1: computed tomography system; 2: X-ray tube; 3: detector; 4: system axis; 5: housing; 6: displaceable patient table; 7: patient; 8: control line for the automatic injection apparatus; 9: arithmetic unit; 10: data and control line; 11: controlled injection unit; 12: intravenous access; 13: stipulated aims for contrast medium concentration; 14-17: enhancement curves; 18: forecast curve; 18+: upper statistical limit of the forecast range of FIG. 18; 18−: lower limit of the statistical forecast range of curve 18; 19, 20: time limits of the observation of a test bolus dose; A: first function constant, substantially indirectly proportional to the width of the test bolus curve; B: second function constant, substantially proportional to the peak of the test bolus curve; b(x,t): concentration profile of the bolus at location x at time t; C: third function constant, proportional to the area under the test bolus curve; $c_0$, enhancement value before the injection of the contrast medium bolus; Erf( ): error function; $F_R$: flow rate of the contrast medium of the correct bolus; $F_T$: flow rate of the contrast medium of the test bolus; $t_{FR}$: forecast instant to form FR; $t_{FT}$: test instant for FT; $t_{0R}$: starting instant for forecasting FR; $t_{0T}$: starting instant for FT; $t_1$–$p_N$: program or program modules; x: location observed.

In detail.

DETAILED DESCRIPTION OF THE EXAMPLE EMBODIMENTS

Figure 1:
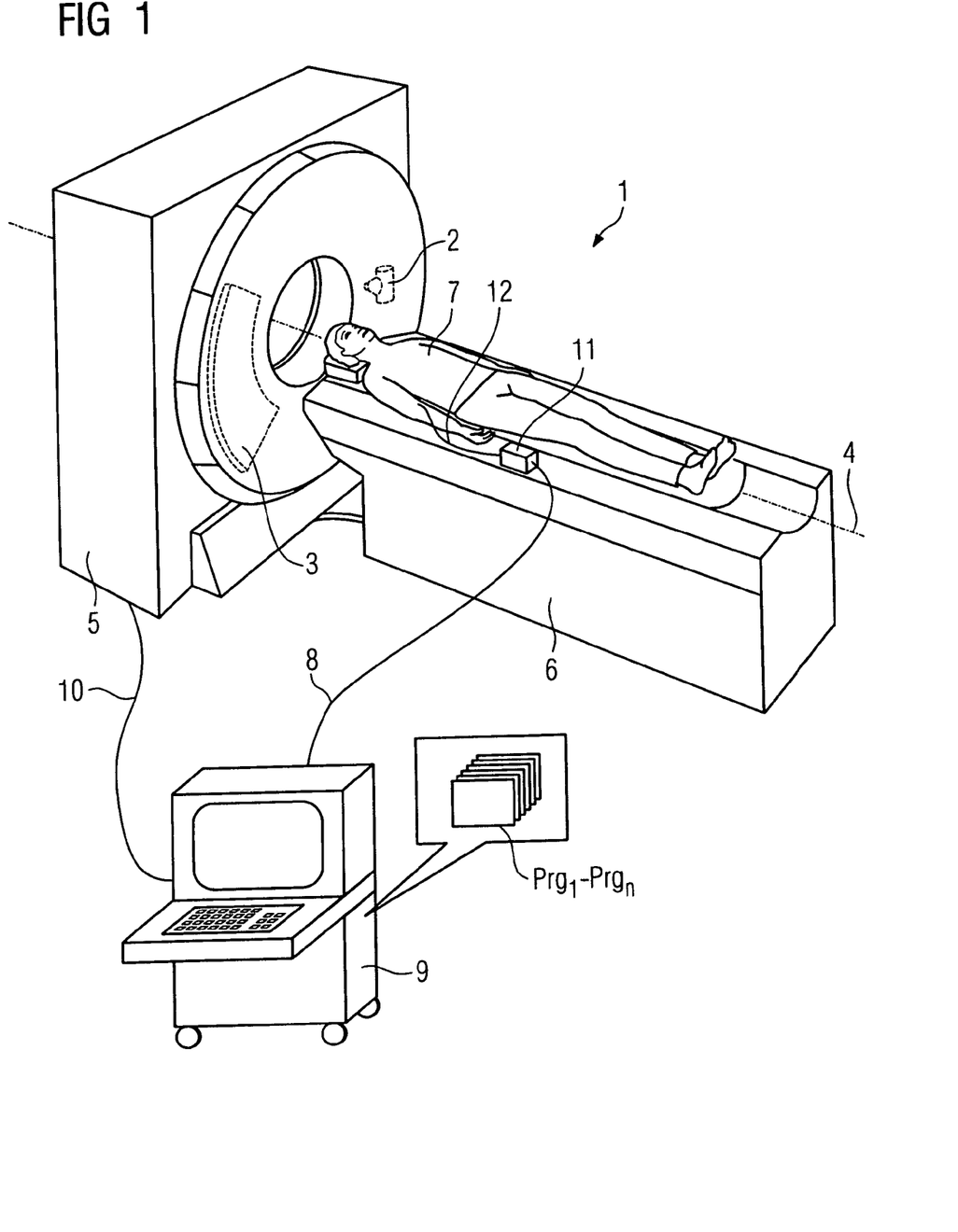
FIG. 1: shows a schematic of a CT system.

FIG. 1 shows an example computed tomography system 1 that is used with the method according to at least one embodiment of the invention and is used in different variants. In the case illustrated, the computed tomography system 1 has an X-ray tube 2 with a detector 3 situated opposite, which are arranged in a rotating fashion on a gantry. During rotation of the X-ray tube 2 and the detector 3, a patient 7 on a patient table 6 is pushed along the system axis 4 past the X-ray tube 2 and the detector 3 such that spiral scanning takes place relative to the patient. The X-ray tube 2 and the detector 3 are located together with the gantry in a housing 5 that is connected to an arithmetic unit 9 via a data and control line 10. In order to inject contrast media, a control line 8 from the arithmetic unit 9 is used to control an injector 11 that injects the contrast medium at the desired flow rate and at the desired instant via an intravenous access 12 to the patient.

Figure 2:
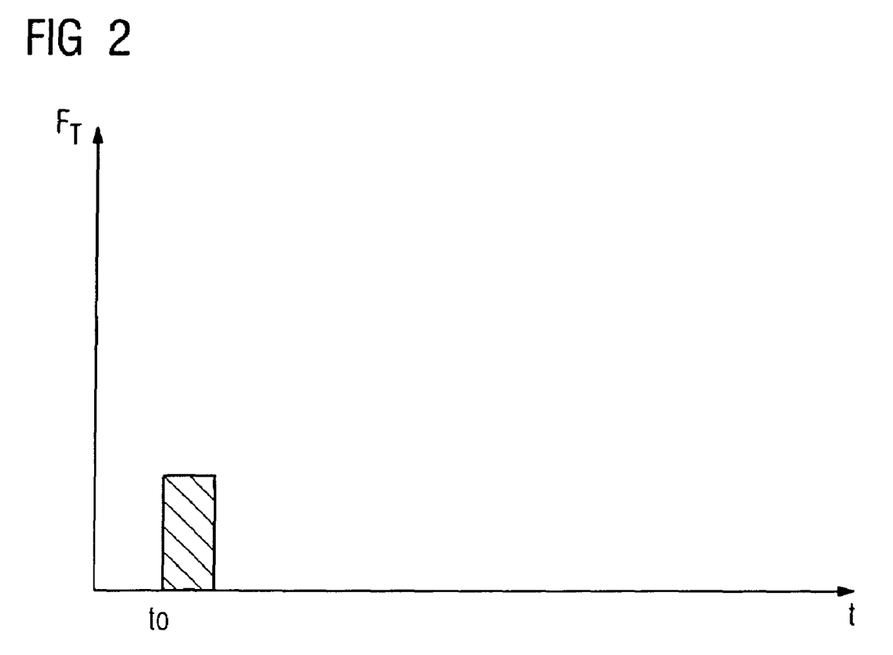
FIG. 2: shows a flow of a test bolus injection.

If a so-called test bolus is injected, this results in a flow rate of the contrast medium at the injector such as is illustrated in FIG. 2. FIG. 2 shows the flow rate $F_T$ above the time axis t. The injection of the test bolus begins at the instant $t_{0T}$ and has a rectangular profile that is illustrated by hatching.

The contrast medium distribution in the body that follows the test bolus injection can be determined on the basis of such a test bolus injection and a test scan carried out during this test bolus injection.

Figure 3:
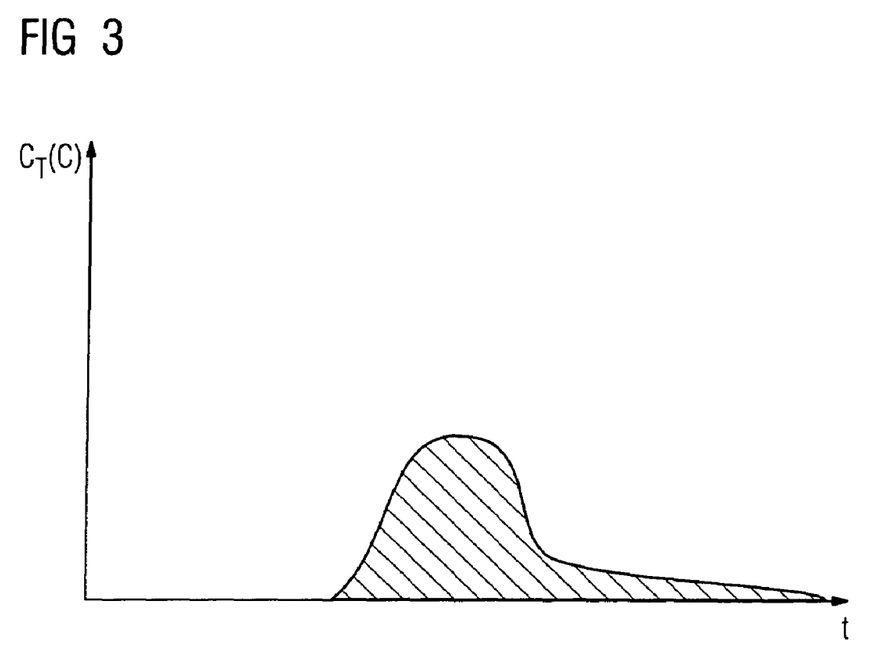
FIG. 3: shows a concentration profile after a test bolus injection.

FIG. 3 shows an enhancement curve, that is to say the pictorial response of the contrast medium at an observed location of the patient, for example an atrium of a heart. Plotted on the ordinate are the concentration values $c_T(X)$ that are correlated with the measured enhancement values from the pictorial illustration. The illustrated curve of the temporally varying concentration of contrast medium at the examined location exhibits a typical sharp rise with a short plateau that corresponds approximately to the duration of the test bolus injection, and a subsequently sharp drop followed by a slowly falling low plateau.

The aim of such a contrast medium dose is to obtain a sufficient contrast medium concentration in the observed region during the tomographic examination with the aid of the computer tomograph in order to ensure a good display, for example, of cardiac arteries. Thus, there is a need for a specific concentration of the contrast medium that permits an appropriate display. At the same time, however, the concentration is not to be excessively high, since the negative biological effect of the contrast medium is to be kept as slight as possible.

Figure 4:
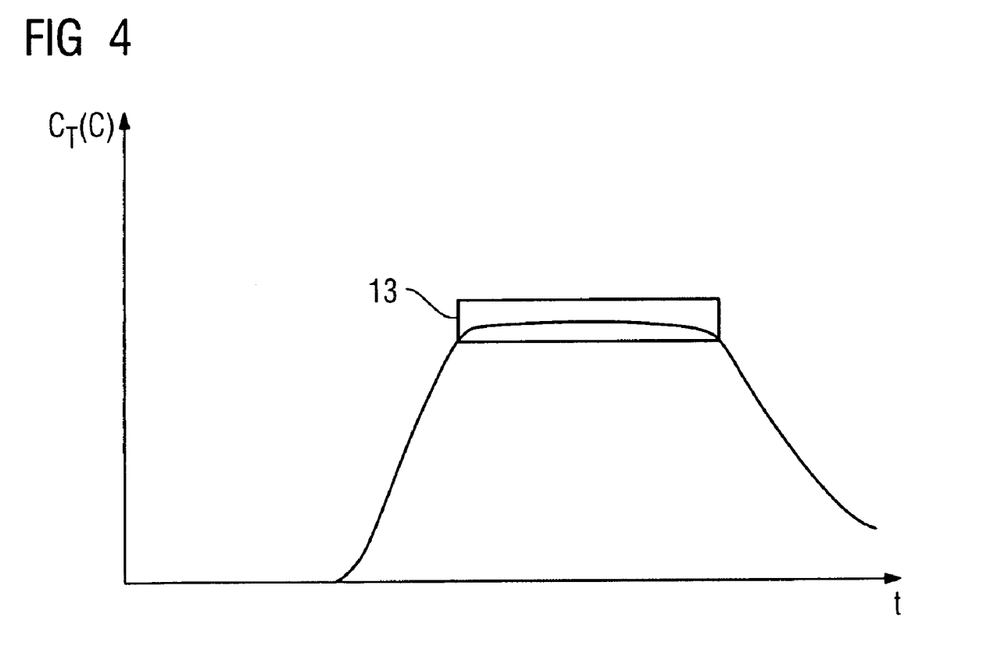
FIG. 4: shows a desired, forecast concentration profile of a correct contrast medium injection.

Such a desired area 13 of the contrast medium concentration during a prescribed time interval that corresponds to the examination interval is illustrated in FIG. 4 as an outlined rectangle 13. The aim now is to use the known test bolus data to perform a correct contrast medium injection that leads in the final analysis to a contrast medium concentration during the scan that is sufficient but not of excessively high profile.

Figure 5:
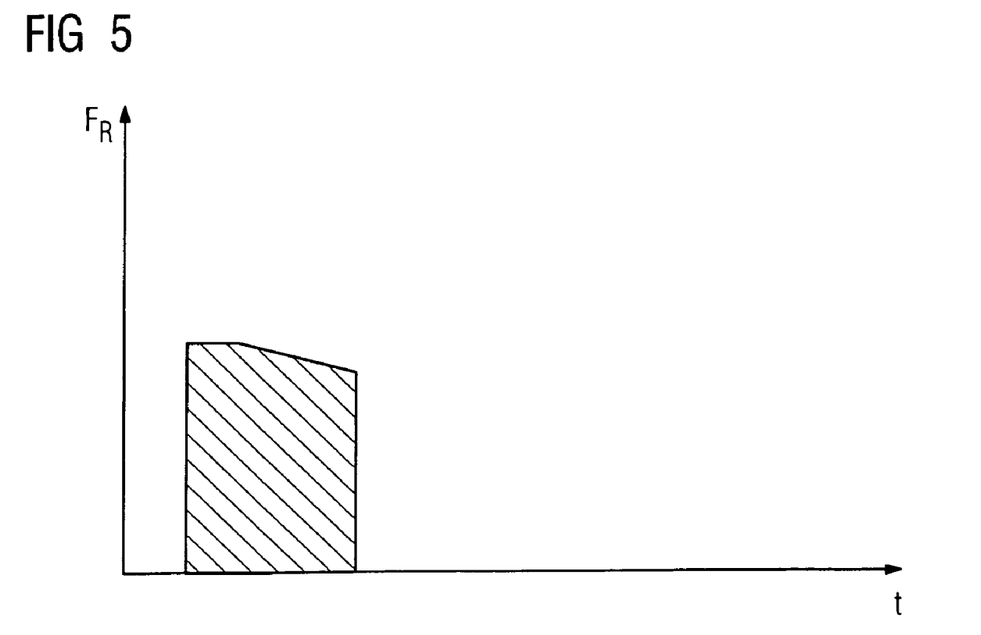
FIG. 5: shows a flow of the correct contrast medium injection relating to FIG. 4.

For example, FIG. 5 illustrates such a profile with reference to the flow rate $F_R$ such that can be found by way of the method according to at least one embodiment of the invention.

Figure 6:
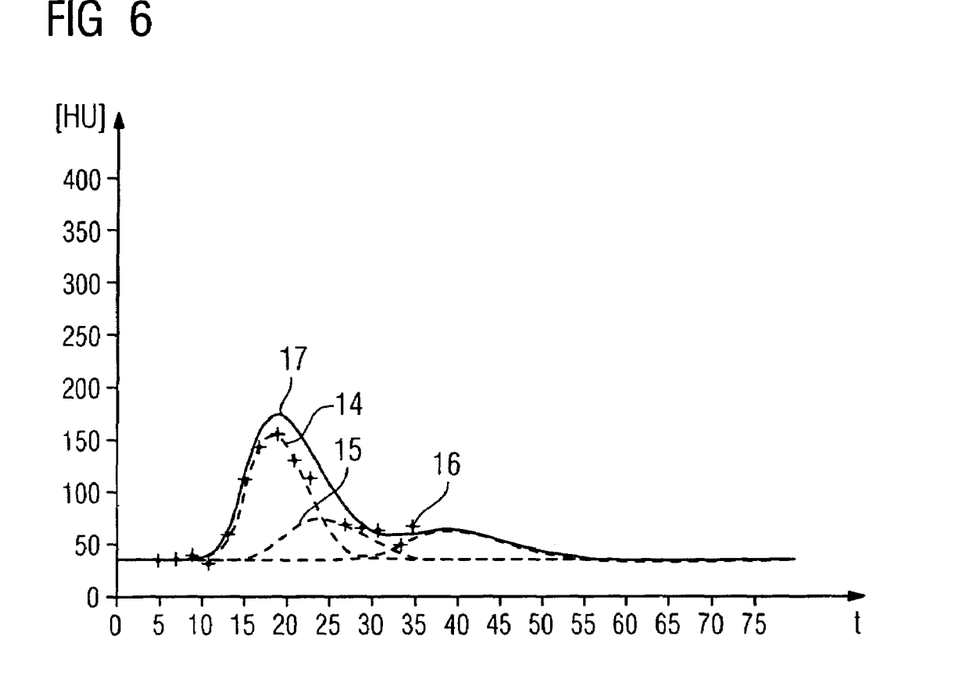
FIG. 6: shows a theoretical profile of enhancement data after a test bolus injection.

FIG. 6 shows a range of measuring points plotted as HU values against time t such as are found in the case of a test bolus—corresponding to FIG. 2—in the region of an atrium of the heart. The time $t_0$ corresponds here to the beginning $t_{0T}$ of the test bolus injection. In addition to the HU values determined on the basis of the test bolus injection, three curves are shown with dashes, the first steep curve 14 corresponding to the direct transmission of the contrast medium from the injection point to the measurement point. The next, and smaller, curve 15 shows decelerating, slower contrast medium, and finally the curve 16 shows the influence based on a recirculation of the contrast medium in the blood circulation. The addition of the curves 14 to 16 then corresponds to the sum of all three effects in the body, and to the profile 17 actually found for the concentration at the observed location x.

Figure 7:
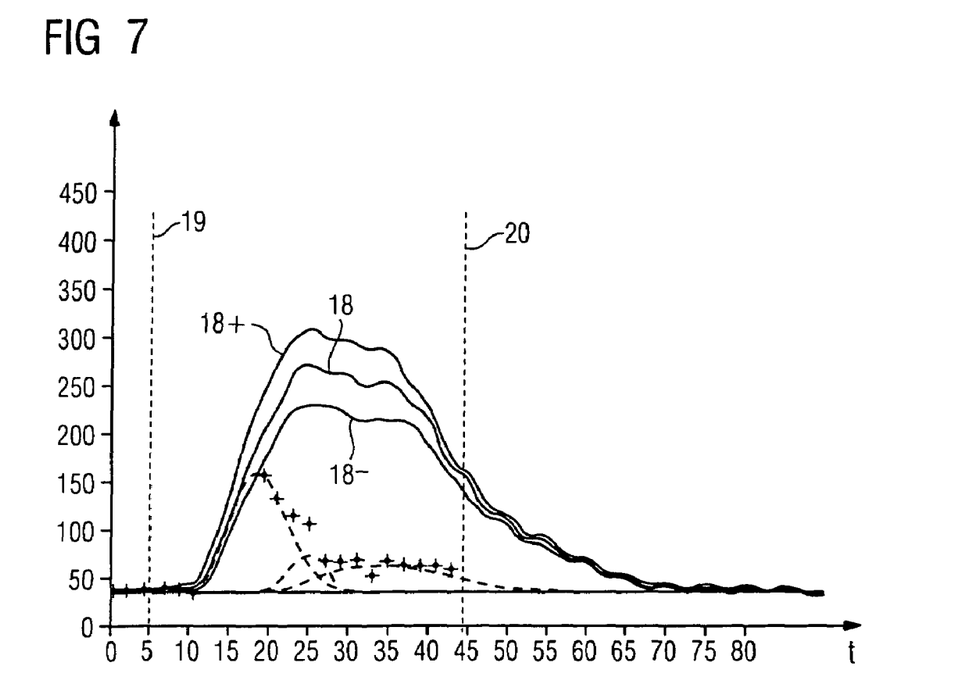
FIG. 7: shows a forecast profile of the enhancement data after a correct contrast medium injection.

If the forecast concentration values, or here enhancement values in HU units, are calculated in advance on the basis of the measured values, illustrated in FIG. 6, of the test bolus and the calculation methods previously shown, the result is a curve 18 as illustrated in FIG. 7. The curve 18+ located thereabove, and the curve 18− situated therebelow respectively limit the confidence interval to be expected statistically. In the example calculation method of at least one embodiment, in which the linear formulation is combined with the physiological formulation, it is possible to forecast the concentration values to be expected even beyond the temporal limits of the measurements of the test bolus—illustrated here by the vertical dashes 19 and 20—, and so the forecast values that go beyond the temporal limit 20 have been approximated in the illustration shown in FIG. 7 by the physiological model.

Figure 8:
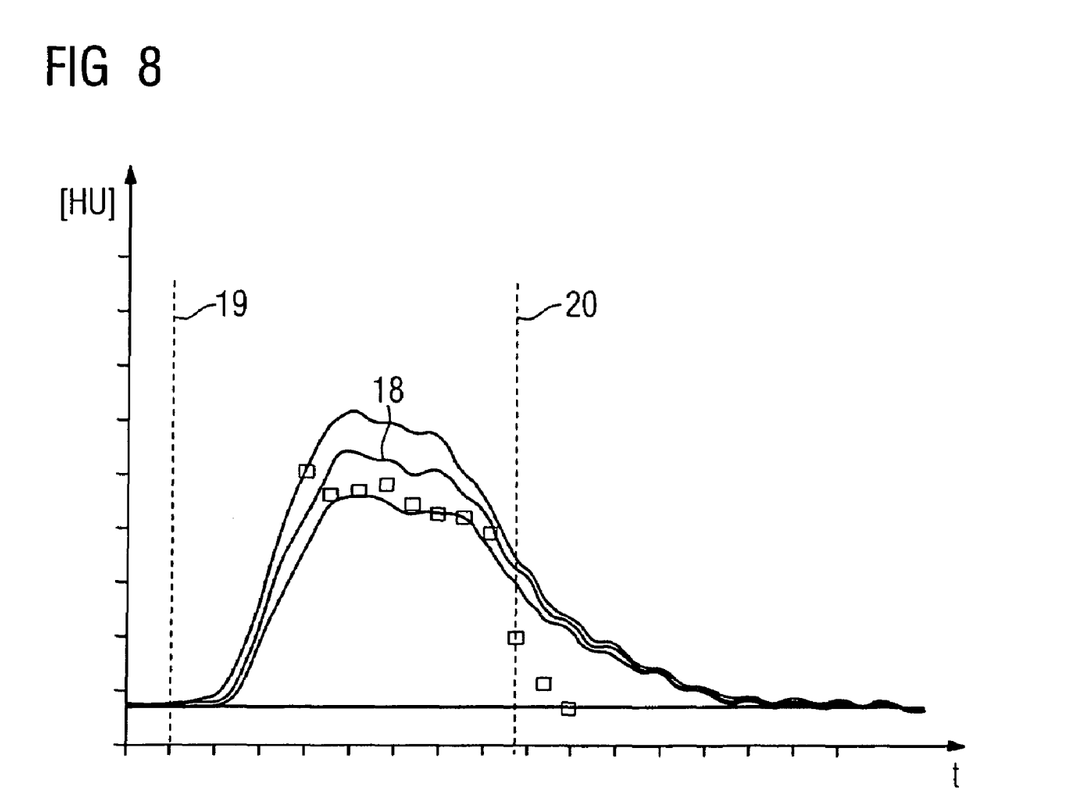
FIG. 8: shows FIG. 7 with additionally represented measured values after the contrast medium injection.

FIG. 8 illustrates a comparison between the values actually determined, shown as open squares, and the theoretically forecast curve 18.

It is self-evident that the abovementioned features of at least one embodiment of the invention can be used not only in the respectively specified combination, but also in other combinations or on their own without departing from the scope of the invention.

It may be pointed out, furthermore, that the method according to at least one embodiment of the invention can be used not only in computed tomography systems, but, for example, also in NMR tomography systems or in conjunction with C bow X-ray systems.

Overall, therefore, the method according to at least one embodiment of the invention enables an improved forecast of enhancement values after contrast medium injections, and thus represents in conclusion an improved possibility of how it is possible to calculate in advance an appropriate contrast medium injection, in particular also the time profile thereof, at a predetermined location in the body of a patient on the basis of given or desired contrast medium concentrations.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for forecasting the contrast medium flow in a living body, comprising:

injecting a defined test bolus with a contrast medium into the body;

observing and determining a time concentration profile of the contrast medium over a limited time period with a number of measuring instants at at least one location in the body with the aid of a tomographic method;

forecasting a time profile of the contrast medium concentration of another contrast medium dose from the measured data obtained via the distribution of the contrast medium, with the aid of a linear cause/effect formulation; and using the following calculation formula for forecasting the time concentration profile $\tilde{c}_R(t)$ of the contrast medium at at least one of the previously measured locations of the body:

$$\tilde{c}_R(t) = \frac{1}{F_T} \sum_{n=-\infty}^{\infty} \int_{-\infty}^{\infty} dt' \tilde{c}_R(t + t_{0T} - n\Delta_T - t') b'_R(t'),$$

in which $\tilde{c}_R(t+t_{0T}-n\Delta_T-t')$ corresponds to the concentration displaced from the instant t to the instant $t+t_{0T}-n\Delta_T-t'$, $F_T$ corresponds to the flow rate of the contrast medium of the test bolus, $b'_R(t')$ corresponds to the time derivative of the profile of the contrast medium bolus administered, t corresponds to the forecast instant, and t' corresponds to the integration variable.

2. The method as claimed in claim 1, wherein a contrast medium injection with constant flow over the injection time is used as test bolus and final bolus to be calculated, and the forecast of the concentration profile $\tilde{c}_R(t)$ is calculated with the aid of the following formula:

$$\tilde{c}_R(t) = \frac{1}{2\pi} \frac{F_R}{F_T} \int_{-\infty}^{\infty} d\xi \exp(-i\xi(t - t_{0R} + t_{0T}))$$

$$(1 - \exp(i\xi\Delta_R)) \sum_{n=0}^{\infty} \exp(in\xi\Delta_T) \tilde{C}_T(\xi)$$

-continued $$= \frac{1}{2\pi} \frac{F_R}{F_T} \sum_{n=0}^{\infty} \int_{-\infty}^{\infty} d\xi (1 - \exp(i\xi\Delta_R))$$

$$\exp(-i\xi(t - t_{0R} + t_{0T} + n\Delta_T))\tilde{C}_T(\xi)$$

$$= \frac{F_R}{F_T} \sum_{n=0}^{\infty} (\tilde{c}_T(t - t_{0R} + t_{0T} - n\Delta_T) -$$

$$\tilde{c}_T(t - t_{FR} + t_{0T} - n\Delta_T))$$

the following designations being used:
$F_T$ flow rate of the contrast medium of the test bolus
$F_R$ flow rate of the contrast medium of the correct bolus
$\xi$ integration variable
$t_{0R}$ starting instant of the correct bolus
$t_{0T}$ starting instant of the test bolus.

3. The method as claimed in claim 1, wherein, in order to forecast instants for which no measured values from a test bolus injection are present, the contrast medium concentration is forecast using a physiological calculation model.

4. The method as claimed in claim 3, wherein the following system of differential equations is used as physiological calculation model:

$$\frac{\partial}{\partial t} b(x, t) + v \frac{\partial}{\partial x} b(x, t) - D \frac{\partial^2}{\partial x^2} b(x, t) = F\delta^{(1)}(x)\Theta(t - t_0)\Theta(t_F - t),$$

the following designations being used:
b(x,t) concentration profile of the bolus at location x at time t,
F flow of the contrast medium,
$\delta^{(1)}$ delta function,
$\Theta(t-t_0)$ Heaviside step function for describing the beginning of the injection,
$\Theta(t_F-t)$ Heaviside step function for describing the end of the injection.

5. The method as claimed in claim 3, wherein in order to forecast instants for which no measured values from a test bolus injection are present, the measured concentration profile is firstly approximated after a test bolus injection with the aid of the following function:

$$b(x, t) = c_0 + C\Theta(t - t_{0T})\left(\Theta(t_{FT} - t)\left(1 - Erf\left(A\frac{B - (t - t_{0T})}{\sqrt{(t - t_{0T})}}\right)\right) + \Theta(t - t_{FT})\left(Erf\left(A\frac{B - (t - t_{FT})}{\sqrt{(t - t_{FT})}}\right)\right) - Erf\left(A\frac{B - (t - t_{0T})}{\sqrt{(t - t_{0T})}}\right)\right)$$

and subsequently the expected concentration profile is estimated using the parameters A, B, C and c_0 thus calculated with the aid of the following formula:

$$b(x, t) = c_0 + C\frac{F_R}{F_T}\Theta(t - t_{0R})\left(\Theta(t_{FR} - t)\left(1 - Erf\left(A\frac{B - (t - t_{0R})}{\sqrt{(t - t_{0R})}}\right)\right) + \Theta(t - t_{FR})\left(Erf\left(A\frac{B - (t - t_{FR})}{\sqrt{(t - t_{FR})}}\right)\right) - Erf\left(A\frac{B - (t - t_{0R})}{\sqrt{(t - t_{0R})}}\right)\right)$$

the following designations being used:
A first function constant, substantially indirectly proportional to the width of the test bolus curve,
B second function constant, substantially proportional to the peak of the test bolus curve,
b(x, t) concentration profile of the bolus at location x at time t,
C third function constant, proportional to the area under the test bolus curve,
$c_0$ enhancement value before the injection of the contrast medium bolus,
Erf( ) error function,
$F_R$ flow rate of the contrast medium of the correct bolus,
$F_T$ flow rate of the contrast medium of the test bolus,
$t_{FR}$ final instant of the correct bolus,
$t_{FT}$ final instant of the test bolus,
$t_{OR}$ starting instant of the correct bolus,
$t_{OT}$ starting instant of the test bolus,
x observed location,
$\Theta$ Heaviside step functions for describing the beginning and the end of the bolus injections.

6. The method as claimed in claim 3, wherein a mean value of the two forecast values is used for instants at which forecasts from the linear model and the physiological model are present.

7. The method as claimed in claim 3, wherein a weighted mean value of the two forecast values is used for instants at which forecasts from the linear model and the physiological model are present.

8. The method as claimed in claim 2, wherein, in order to forecast instants for which no measured values from a test bolus injection are present, the contrast medium concentration is forecast using a physiological calculation model.

9. The method as claimed in claim 8, wherein the following system of differential equations is used as physiological calculation model:

$$\frac{\partial}{\partial t} b(x, t) + v \frac{\partial}{\partial x} b(x, t) - D \frac{\partial^2}{\partial x^2} b(x, t) = F\delta^{(1)}(x)\Theta(t - t_0)\Theta(t_F - t),$$

the following designations being used:
b(x,t) concentration profile of the bolus at location x at time t,
F flow of the contrast medium,
$\delta^{(1)}$ delta function,
$\Theta(t-t_0)$ Heaviside step function for describing the beginning of the injection,
$\Theta(t_F-t)$ Heaviside step function for describing the end of the injection.

10. The method as claimed in claim 8, wherein in order to forecast instants for which no measured values from a test bolus injection are present, the measured concentration profile is firstly approximated after a test bolus injection with the aid of the following function:

$$b(x, t) = c_0 + C\Theta(t - t_{0T})\left(\Theta(t_{FT} - t)\left(1 - Erf\left(A\frac{B - (t - t_{0T})}{\sqrt{(t - t_{0T})}}\right)\right) + \Theta(t - t_{FT})\left(Erf\left(A\frac{B - (t - t_{FT})}{\sqrt{(t - t_{FT})}}\right)\right) - Erf\left(A\frac{B - (t - t_{0T})}{\sqrt{(t - t_{0T})}}\right)\right)$$

and subsequently the expected concentration profile is estimated using the parameters A, B, C and c_0 thus calculated with the aid of the following formula:

$$b(x,t) = c_0 + C\frac{F_R}{F_T}\Theta(t-t_{0R})\left(\Theta(t_{FR}-t)\left(1-Erf\left(A\frac{B-(t-t_{0R})}{\sqrt{(t-t_{0R})}}\right)\right)+\right.$$
$$\left.\Theta(t-t_{FR})\left(Erf\left(A\frac{B-(t-t_{FR})}{\sqrt{(t-t_{FR})}}\right)\right)-Erf\left(A\frac{B-(t-t_{0R})}{\sqrt{(t-t_{0R})}}\right)\right)$$

the following designations being used:
A first function constant, substantially indirectly proportional to the width of the test bolus curve,
B second function constant, substantially proportional to the peak of the test bolus curve,
b(x, t) concentration profile of the bolus at location x at time t,
C third function constant, proportional to the area under the test bolus curve,
$c_0$ enhancement value before the injection of the contrast medium bolus,
Erf( ) error function,
$F_R$ flow rate of the contrast medium of the correct bolus,
$F_T$ flow rate of the contrast medium of the test bolus,
$t_{FR}$ final instant of the correct bolus,
$t_{FT}$ final instant of the test bolus,
$t_{0R}$ starting instant of the correct bolus,
$t_{0T}$ starting instant of the test bolus,
x observed location,
Θ Heaviside step functions for describing the beginning and the end of the bolus injections.

11. The method as claimed in claim 4, wherein in order to forecast instants for which no measured values from a test bolus injection are present, the measured concentration profile is firstly approximated after a test bolus injection with the aid of the following function:

$$b(x,t) = c_0 + C\Theta(t-t_{0T})\left(\Theta(t_{FT}-t)\left(1-Erf\left(A\frac{B-(t-t_{0T})}{\sqrt{(t-t_{0T})}}\right)\right)+\right.$$
$$\left.\Theta(t-t_{FT})\left(Erf\left(A\frac{B-(t-t_{FT})}{\sqrt{(t-t_{FT})}}\right)\right)-Erf\left(A\frac{B-(t-t_{0T})}{\sqrt{(t-t_{0T})}}\right)\right)$$

and subsequently the expected concentration profile is estimated using the parameters A, B, C and c_0 thus calculated with the aid of the following formula:

$$b(x,t) = c_0 + C\frac{F_R}{F_T}\Theta(t-t_{0R})\left(\Theta(t_{FR}-t)\left(1-Erf\left(A\frac{B-(t-t_{0R})}{\sqrt{(t-t_{0R})}}\right)\right)+\right.$$
$$\left.\Theta(t-t_{FR})\left(Erf\left(A\frac{B-(t-t_{FR})}{\sqrt{(t-t_{FR})}}\right)\right)-Erf\left(A\frac{B-(t-t_{0R})}{\sqrt{(t-t_{0R})}}\right)\right)$$

the following designations being used:
A first function constant, substantially indirectly proportional to the width of the test bolus curve,
B second function constant, substantially proportional to the peak of the test bolus curve,
b(x, t) concentration profile of the bolus at location x at time t,
C third function constant, proportional to the area under the test bolus curve,
$c_0$ enhancement value before the injection of the contrast medium bolus,
Erf( ) error function,
$F_R$ flow rate of the contrast medium of the correct bolus,
$F_T$ flow rate of the contrast medium of the test bolus,
$t_{FR}$ final instant of the correct bolus,
$t_{FT}$ final instant of the test bolus,
$t_{0R}$ starting instant of the correct bolus,
$t_{0T}$ starting instant of the test bolus,
x observed location,
Θ Heaviside step functions for describing the beginning and the end of the bolus injections.

12. The method as claimed in claim 4, wherein a mean value of the two forecast values is used for instants at which forecasts from the linear model and the physiological model are present.

13. The method as claimed in claim 4, wherein a weighted mean value of the two forecast values is used for instants at which forecasts from the linear model and the physiological model are present.

14. The method as claimed in claim 5, wherein a mean value of the two forecast values is used for instants at which forecasts from the linear model and the physiological model are present.

15. The method as claimed in claim 5, wherein a weighted mean value of the two forecast values is used for instants at which forecasts from the linear model and the physiological model are present.

16. The method as claimed in claim 1, wherein the injecting of a defined test bolus with a contrast medium is done intravenously and with a known injection flow profile, into a blood vessel of the body.

17. A computer program stored on a computer program product and adapted to, when executed on a computer following the injection of a defined test bolus with a contrast medium into the body, cause the computer to carry out steps of:
observing and determining a time concentration profile of the contrast medium over a limited time period with a number of measuring instants at at least one location in the body with the aid of a tomographic method;
forecasting a time profile of the contrast medium concentration of another contrast medium dose from the measured data obtained via the distribution of the contrast medium, with the aid of a linear cause/effect formulation; and
using the following calculation formula for forecasting the time concentration profile $\tilde{c}_R(t)$ of the contrast medium at at least one of the previously measured locations of the body;

$$\tilde{c}_R(t) = \frac{1}{F_T}\sum_{n=-\infty}^{\infty}\int_{-\infty}^{\infty}dt'\tilde{c}_R(t+t_{0T}-n\Delta_T-t')b'_R(t'),$$

in which
$\tilde{c}_R(t+t_{0T}-n\Delta_T-t')$ corresponds to the concentration displaced from the instant t to the instant $t+t_{0T}-n\Delta_T-t'$,
$F_T$ corresponds to the flow rate of the contrast medium of the test bolus,
$b'_R(t')$ corresponds to the time derivative of the profile of the contrast medium bolus administered.
t corresponds to the forecast instant, and
t' corresponds to the integration variable.

18. A computer readable medium including program segments for, when executed on a computer following the injection of a defined test bolus with a contrast medium into the body, causing the computer to implement steps of:
observing and determining a time concentration profile of the contrast medium over a limited time period with a number of measuring instants at at least one location in the body with the aid of a tomographic method;

forecasting a time profile of the contrast medium concentration of another contrast medium dose from the measured data obtained via the distribution of the contrast medium, with the aid of a linear cause/effect formulation; and using the following calculation formula for forecasting the time concentration profile $\tilde{c}_R(t)$ of the contrast medium at at least one of the previously measured locations of the body:

$$\tilde{c}_R(t) = \frac{1}{F_T} \sum_{n=-\infty}^{\infty} \int_{-\infty}^{\infty} dt' \tilde{c}_R(t + t_{0T} - n\Delta_T - t') b'_R(t'),$$

in which $\tilde{c}_R(t+t_{0T}-n\Delta_T-t')$ corresponds to the concentration displaced from the instant t to the instant $t+t_{0T}-n\Delta_T-t'$, $F_T$ corresponds to the flow rate of the contrast medium of the test bolus, $b'_R(t')$ corresponds to the time derivative of the profile of the contrast medium bolus administered.

t corresponds to the forecast instant, and t' corresponds to the integration variable.

* * * * *